(12) United States Patent  
Krishnan et al.

(10) Patent No.: US 12,277,718 B2
(45) Date of Patent: Apr. 15, 2025

(54) COMPUTER-IMPLEMENTED METHOD FOR VISUALIZATION OF AN ELONGATED ANATOMICAL STRUCTURE

(71) Applicant: KONINKLIJKE PHILIPS N.V., Eindhoven (NL)

(72) Inventors: Karthik Krishnan, Bangalore (IN); Celine Firtion, Surat (IN); Subhendu Seth, Bangalore (IN); Pallavi Vajinepalli, Bangalore (IN); David Nigel Roundhill, Woodinville, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 381 days.

(21) Appl. No.: 17/915,183

(22) PCT Filed: Mar. 24, 2021

(86) PCT No.: PCT/EP2021/057514
§ 371 (c)(1),
(2) Date: Sep. 28, 2022

(87) PCT Pub. No.: WO2021/197948
PCT Pub. Date: Oct. 7, 2021

(65) Prior Publication Data
US 2023/0124879 A1 Apr. 20, 2023

Related U.S. Application Data

(60) Provisional application No. 63/004,547, filed on Apr. 3, 2020.

(51) Int. Cl.
*G06T 7/30* (2017.01)
*A61B 8/00* (2006.01)
*A61B 8/08* (2006.01)
*G06T 3/10* (2024.01)
*G06T 7/00* (2017.01)

(52) U.S. Cl.
CPC .............. *G06T 7/30* (2017.01); *A61B 8/0866* (2013.01); *A61B 8/0875* (2013.01); *A61B 8/463* (2013.01);
(Continued)

(58) Field of Classification Search
None
See application file for complete search history.

(56) References Cited

U.S. PATENT DOCUMENTS 10,460,508 B2   10/2019   Zhan et al.
2008/0287796 A1  11/2008   Kiraly et al.
(Continued)

FOREIGN PATENT DOCUMENTS

WO   2005048198 A1   5/2005
WO   2015063632 A2   5/2015
WO   2019016064 A1   1/2019

OTHER PUBLICATIONS

International Search Report and Written Opinion for PCT/EP2021/057514; Mailing date: Jul. 9, 2021, 10 pages.
(Continued)

*Primary Examiner* — Mark R Milia

(57) ABSTRACT

A computer-implemented method for visualization of an elongated anatomical structure (20), for example of a fetal spine using ultrasound is provided. The method comprising the steps of: receiving a plurality of 3D ultrasound image volumes, each image volume depicting at least a portion of an elongated anatomical structure (20); on each 3D ultrasound image volume, automatically or semi-automatically fitting a parametric curve (30) to the depicted portion of the elongated anatomical structure, the parametric curve being defined by curve parameters; reformatting each 3D ultrasound image volume by applying a transformation which straightens the parametric curve along at least one axis, so as to generate a plurality of reformatted image volumes and
(Continued)

reformatted parametric curves (32, 34); registering the reformatted image volumes with one another by determining the joining point of their respective parametric curves; and fusing the reformatted image volumes with one another to yield a fused image depicting the whole elongated anatomical structure or a larger portion thereof than the 3D ultrasound image volumes.

15 Claims, 10 Drawing Sheets

(52) U.S. Cl.
CPC .......... *A61B 8/483* (2013.01); *A61B 8/5253* (2013.01); *G06T 3/10* (2024.01); *G06T 7/0012* (2013.01); *G06T 2207/10136* (2013.01); *G06T 2207/20221* (2013.01); *G06T 2207/30012* (2013.01); *G06T 2207/30044* (2013.01)

(56) References Cited

U.S. PATENT DOCUMENTS

| | | | | |
|---|---|---|---|---|
| 2011/0129137 | A1* | 6/2011 | Tian | G06T 19/00 73/632 |
| 2020/0015777 | A1* | 1/2020 | Ciofolo-Veit | A61B 8/463 |
| 2021/0202069 | A1* | 7/2021 | van der Veen | G16H 50/20 |

OTHER PUBLICATIONS

Hanaoka, S. et al., "Automated segmentation method for spinal column based on a dual elliptic column model and its application for virtual spinal straightening", J Comput Assist Tomogr, 2010, vol. 34, No. 1, pp. 156-162.

Kretschmer, J. et al., "ADR—Anatomy-Driven Reformation", IEEE Transactions on Visualization and Computer Graphics, 2014, vol. 20, No. 12, 10 pages.

Gilboa et al., "Vertebral Anomalies", Chapter 17, Book Ultrasonography of the PreNatal Brain, 3rd Ed, McGraw Hill Medical, 2015, Abstract Only.

Wilson, R.D. et al., "Prenatal Screening, Diagnosis, and Pregnancy Management of Fetal Neural Tube Defects", J Obstet Gynaecol Can, 2021, vol. 43, No. 1, pp. 124-139.

Harrison, L.A. et al., "Abnormal Spinal Curvature in the Fetus", J Ultrasound Med., 1992, vol. 11, pp. 473-479.

De Biasio, P. et al., "Spine length measurement in the first trimester of pregnancy", Prenat Diagn., 2002, vol. 22, pp. 818-822.

Sepulveda, W. et al., "Fetal spinal anomalies in a first-trimester sonographic screening program for aneuploidy", Prenat Diagn., 2011, vol. 31, p. 107-114.

Kanitsar, A. et al., "CPR—Curved Planar Reformation", IEEE Visualization, 2002, pp. 37-44.

* cited by examiner

COMPUTER-IMPLEMENTED METHOD FOR VISUALIZATION OF AN ELONGATED ANATOMICAL STRUCTURE

CROSS-REFERENCE TO PRIOR APPLICATIONS

This application is the U.S. National Phase application under 35 U.S.C. § 371 of International Application No. PCT/EP2021/057514, filed on Mar. 24, 2021, which claims the benefit U.S. Provisional Patent Application No. 63/004,547, filed on Apr. 3, 2020. These applications are hereby incorporated by reference herein.

FIELD OF THE INVENTION

The invention relates to a computer-implemented method for visualization of an elongated anatomical structure, in particular a fetal spine, using ultrasound, a computer program, an image evaluation device configured to perform the inventive method, and an ultrasound system.

BACKGROUND OF THE INVENTION

Ultrasound (US) is the most widely used diagnostic imaging modality for visualizing a fetus. At least three ultrasound examinations, during the first, second and third trimesters of a pregnancy are performed and are recommended by ISUOG (International Society of Ultrasound in Obstetrics & Gynecology) and AIUM (American Institute of Ultrasound in Medicine) guidelines, with additional scans typically performed for high risk pregnancies.

In such context, early detection of fetal spinal anomalies allows for parental counselling and appropriate obstetrical management. Typically, the fetal spine consists of the following segments: cervical (7 vertebra), thoracic (12 vertebra), lumbar (5 vertebra), sacral (5 vertebra) segments and ends with the coccyx. Meticulous evaluation of the fetal spine and all its vertebra is desirable in any obstetrical ultrasound examination, since discovery of a spinal anomaly significantly affects obstetrical management.

The primary screening test for the detection of fetal structural abnormalities such as vertebral body malformations (hemivertebrae, butterfly vertebrae, etc.), neural tube defects (spina bifida and other myelomeningocele) and fetal scoliosis, is an anatomical ultrasound with detailed fetal spinal imaging and assessment performed during the second trimester of the pregnancy. With the right tools, several abnormalities can be detected in the first trimester of pregnancy but not all due to poor ossification of the spine at that early age.

Fetal scoliosis is a complex congenital malformation and is associated with a number of congenital abnormalities. The prognosis for fetuses with abnormal spinal curvature generally is determined from the prognosis of the underlying malformation, and usually it is poor. Because of the poor prognosis of many of the associated anomalies, as many as 60% elect pregnancy termination. The middle of the second to early third trimester is the ideal time to identify abnormal spinal curvature as there is sufficient spinal ossification without the fetal crowding late in pregnancy that makes the spine difficult to image. Detection requires careful back and forth longitudinal scanning in both coronal and parasagittal planes. However, scoliosis detection in second and early third trimesters is often challenging due to an inability to obtain longitudinal images of the entire spine with the restricted field-of-view of ultrasound probes.

As mention above, early detection of spinal abnormalities is a challenge. In the first trimester, focused sonographic examination of the fetal spine is not part of the ISUOG or AIUM guidelines, primarily because of the poor ossification and size of the fetal spine at this gestational age which hinders sonographic examination. In addition, poor visualization of the fetal spine in the first trimester due to maternal habitus and an unfavorable fetal position has been reported in approximately 15% of the cases. Spulveda et al. reviewed in "*Fetal spinal anomalies in a first-trimester sonographic screening program for aneuploidy*", Prenat Diagn. 2011 January; 31(1):107-14 the sonographic features of spinal anomalies in first-trimester fetuses and found that the type of spinal abnormality detected is different when comparing the first and the second trimesters. In the second trimester, spina bifida is by far the most commonly detected anomaly, while in the first trimester study, it was severe kyphoscoliosis. Their first trimester abnormalities were associated with poor perinatal outcomes. Almost all cases of body stalk anomaly, but less than half the cases of spina bifida, can be detected in the first trimester. The spinal length has been found to be a good indicator of fetal growth and shows a high correlation with CRL and biparietal diameter in the first trimester. Therefore, it seems to be crucial to perform an ultrasound examination of the spine during the second or third trimester of pregnancy. However, the restricted field-of-view of ultrasound probes makes the computation of spinal length and the identification and analysis of the different vertebral segments difficult in fetuses in the second or third trimester of pregnancy.

Thus, there is a need for efficiently generating an image of the whole fetal spine or a larger portion of the spine at a later stage of pregnancy using ultrasound, wherein the image may be used for further detailed assessment of the fetal spine.

US 2008/0287796 A1 discloses a method and a system for visualizing the spine in 3D medical images. A spinal cord centerline is automatically determined in a 3D medical image volume, such as a CT volume. A reformatted image volume is then generated based on the spinal cord centerline. The reformatted image volume can be a straightened spine volume or a Multi-planar Reconstruction (MPR) based volume that follows the natural curve of the spine. The reconstructed volume can be displayed as 2D slices or 3D volume renderings.

WO 2015/063632 A2 discloses a method which includes obtaining first image data that includes voxel representing a structure of interest. The structure of interest includes a plurality of different sub-structures. The method further includes segmenting a volume of the first image data that includes only a single sub-structure for each of the plurality of different sub-structures. The method further includes creating a different local coordinate system for each of the different sub-structures for each of the volumes. The method further includes visually presenting the structure of interest through separate visual presentations of sets of reformatted images for each of the individual plurality of different sub-structures. A set of reformatted images for a sub-structure includes different cut planes generated from a corresponding segmented volume of the segmented volumes and the local coordinate system for the sub-structure.

WO 2005 048198 A1 relates to a method and a corresponding apparatus for visualization of a tubular structure of an object by use of a 3D image data set of said object. In order to provide a more efficient and illustrative visualization a method is proposed comprising the steps of:—generating and visualizing a curved planar reformation view from a symbolic pathway view of said tubular structure, said symbolic pathway view representing said tubular structure and the pathway points of said symbolic pathway being assigned with their 3D spatial position data, and—generating and visualizing at least one planar view of said object through a viewing point of said tubular structure selected in said curved planar reformation view or said symbolic pathway view. However, the problem mentioned above remains, namely that the whole fetal spine or a larger portion of the spine cannot be sufficiently displayed in one image so as to analyze the spine for a variety of malformations.

OBJECT OF THE INVENTION

It is therefore an object of the invention to provide a computer-implemented method for efficiently generating a visualization of an elongated anatomical structure, which cannot be visualised in a single ultrasound Field of View, such as a fetal spine using ultrasound that is captured at the second to early third trimester of a pregnancy and which can be used for detailed malformation assumption. It is also an object of the invention to provide a respective computer program, an image evaluation device configured to execute an embodiment of the inventive method and an ultrasound system.

SUMMARY OF THE INVENTION

To better address one or more of the above-identified concerns, in a first aspect of the invention, a computer-implemented method for visualization of a fetal spine using ultrasound is provided, the method comprising the steps of:
receiving a plurality of 3D ultrasound image volumes, each image volume depicting at least a portion of an elongated anatomical structure having a curved longitudinal extension;
on each 3D ultrasound image volume, automatically or semi-automatically fitting a parametric curve to the depicted portion of the elongated anatomical structure along its longitudinal extension, the parametric curve being defined by curve parameters;
reformatting each 3D ultrasound image volume by applying a transformation which straightens the parametric curve along at least one axis, so as to generate a plurality of reformatted image volumes and reformatted parametric curves;
registering the reformatted image volumes with one another by determining the joining point of their respective parametric curves; and
fusing the reformatted image volumes with one another to yield a fused image depicting the whole elongated anatomical structure or a larger portion thereof than the 3D ultrasound image volumes.

In other words, the present invention may provide a method for visualizing of the whole elongated anatomical structure, or a large portion thereof, from multiple ultrasound volumes via contextual (e.g. based on the elongated structure) fusion so as to be able to immediately assess the complete anatomical structure. The three-dimensional (3D) ultrasound image volumes may be 3D medical images of a portion of a patient's body. The 3D ultrasound image volumes may be received from an image acquisition device in real time after the image volumes have been acquired from a patient, a pregnant woman, for example. The 3D ultrasound image volumes may also be received by inputting or loading image volumes that were previously acquired and stored, for example on storage or memory of a computer system. Further, the 3D ultrasound image volumes may be acquired during an examination at a hospital, for example, and then may be send to another location to a data processing service center, for example, for executing the inventive method.

The elongated anatomical structure has a curved longitudinal extension, such that the parametric curve fitted thereto will usually not be straight. The anatomical structure may be any elongated structure within the human or animal body, in particular a larger structure which cannot be captured in the Field of View (FoV) of a single ultrasound image, such as the spine of a fetus in the second or third trimester, the spine of a child or adult, a bone structure, a limb or part of a limb, a blood vessel, or a part of the intestine. Preferably, the elongated anatomical structure has a longitudinal extension, which is the direction in which it is elongated. In the case of a spine, the longitudinal extension may e.g. run along the central neural tube. In case of a blood vessel, the longitudinal extension may be in the direction of blood flow.

Herein, the invention will be explained with reference to an example where the elongated anatomical structure is the fetal spine. However, the invention is also applicable to other elongated anatomical structures.

In an embodiment, the method comprises a step of acquiring a plurality of 3D ultrasound image volumes from a subject, in particular a pregnant woman, each image volume depicting at least portion of the fetal spine of a fetus. Preferably, the fetus will be in the second or third trimester, so that sufficient ossification of the spine has taken place.

The 3D ultrasound image volumes may be acquired using a variety of ultrasound devices. For example, a 3D image volume may be collected by acquiring a series of two-dimensional (2D) ultrasound images, recording the transducer orientation for each image/slice and subsequently generating 3D ultrasound image volumes based on the 2D images and the transducer orientation. Alternatively, the 3D ultrasound image volumes may be directly captured by using a matrix array transducer that uses beam steering to sample points throughout a pyramid shaped volume (i.e. a 3D ultrasound image volume). The several 3D ultrasound image volumes may be captured during the same examination, in particular substantially at the same time, preferably at the same day. Further, each of the 3D ultrasound image volumes may include a different part of the same fetal spine. Each 3D ultrasound image volume may include at least one vertebra of the fetal spine. Preferably the Field-of-View (FoV) of the 3D ultrasound image volumes may overlap each other at least partly, that is, some parts of the fetal spine are depicted on several of the 3D ultrasound image volumes. The overlapping amount may be in a range between 10 and 50 percent of the size of the 3D ultrasound image volume, preferably in a range between 20 and 40 percent and more preferably about 30 percent.

On each 3D ultrasound image volume, a parametric curve is automatically or semi-automatically fitted to the depicted portion of the elongated anatomical structure along its longitudinal extension or direction. In case of a spine, the parametric curve may be fitted to the centerline of the depicted spine portion. The parametric curve may define the elongated anatomical structure as a function of one or more independent variables called curve parameters, and hence may express coordinates of points that define the geometrical extension of the elongated anatomical structure in each of the 3D ultrasound image volumes. The parametric curve may be called a parametric representation or parameterization of the elongated anatomical structure. The advantage of using a parametric curve as an approximation is that it is a simple definition of the longitudinal extension. Further, by using the curve parameters, a parametrized fusion of the several image volumes can be carried out, as described below. The parametric curves preferably define the elongated anatomical structure in three dimensions, e.g. in the coordinates of the 3D image volume.

The parametric curve is usually continuous and preferably (but not necessarily) differentiable, i.e. smooth. In an embodiment, the parametric curve has a pre-determined format, for example it is pre-determined to be a polynomial, exponential or trigonometric function, including variations or linear combinations thereof. For example, it may be a polynomial of $n^{th}$ degree, or more preferred it is pre-determined to be a spline function, preferably of degree 3 (a cubic spline function). A spline function is a function defined piecewise by polynomials. If the polynomial pieces each have degree of at most n, then the spline is said to be of degree n. The places where the pieces meet are termed "knots".

The curve parameters are the parameters defining the curve. For a spline function, the parameters include for example the positions of the knots and the parameters of the polynomial pieces.

In case the elongated anatomical structure is the spine of a fetus, the parametric curve may be an approximation of the centerline of the spine, i.e. the line that runs along the central neural tube of the spine.

The parametric curve may be fitted automatically to the depicted portion of the elongated anatomical structure, so that no user interaction is required. For example, the lumen of a blood vessel, the neural tube or the segments of a spine may be identified by suitable segmentation techniques and a parametric curve fitted thereto. For example, the neural tube may be identified automatically or by user interaction, and the parametric curve of pre-determined format may be fitted thereto, thereby determining the curve parameters. In another embodiment, the centerline of the spine may be identified using key point estimation using artificial intelligence.

In another embodiment, the parametric curve is generated semi-automatically, meaning that some user interaction is required. For example, the user may review a parametric curve generated automatically, for example by looking at the parametric curve overlaid on a representation of the 3D image volume on a screen and correct the parametric curve where necessary.

Curve parameters may be determined by selecting control points on the elongated anatomical structure, e.g. on the fetal spine (or within the central neural tube) semi-automatically or automatically, and fitting a (pre-determined) parametric curve to the selected control points. Preferably, the selected points are defined at portions of the elongated anatomical structure, for example, at each vertebra of the fetal spine, which are easily visible within the 3D ultrasound image volumes.

According to the invention, the parametric curve is used for a reformation of each of the 3D ultrasound image volumes by applying a transformation which straightens the parametric curve along at least one axis, so as to generate a plurality of reformatted image volumes (including reformatted parametric curves). One may also say that the parametric curve is straightened in at least one direction. In a special embodiment, the reformatted parametric curve may be completely straight (straight line), in other embodiments, the parametric curve is only partially straightened, for example only in one direction, as explained in more detail below. In the reformatted image volumes, the elongated anatomical structure is "unwarped" at least to some degree. Thereby, assessment of the elongated anatomical structure is considerably simplified.

The reformation may be performed as follows: First of all, the desired transformation of the parametric curve is determined, which may be an operation/transformation which straightens the curve in at least one direction, examples of which are given below. The transformation may be defined based on the parametric curve alone, but in some embodiments also takes into account the intensity values of the 3D image volume, e.g. the 3D image volume is analyzed to determine the orientation in which the parametric curve is straightened. The transformation may then be performed on the parametric curve, resulting in a reformatted parametric curve, which is preferably also defined by curve parameters. Also, the transformation itself may be defined, either algebraically or by means of a transformation matrix.

Then, the dimensions (size) of the reformatted image volume, also referred to as output image or output volume, may be defined, wherein generally the z-axis corresponds to the longitudinal direction of the anatomical structure, i.e. along the parametric curve, and the x- and y-axes are (locally) perpendicular thereto. In one embodiment, the y-axis is a horizontal (left-right) axis of the fetus. The third axis (x-axis) may be in depth direction, perpendicular to the other two axes, and may roughly correspond to an anteroposterior axis of the fetus. The size of the reformatted image in z-direction may be calculated from the parametric curve, whereas the extensions in x- and y-directions may be freely selected according to the visualisation needs. In the example of a fetal spine, the size in y-direction may be 2 to 3 cm, so as to cover the fetal spine including the spinous processes and at least a part of the ribs extending therefrom. The size in x-direction (depth) may be selected to be only one pixel, in which case the output volume is a two-dimensional (2D) output image. If the size of the output image in depth direction is only one or a few (e.g. up to 10) pixels, this corresponds to a "thin-slab" transformation. Thin slab reformations allow one to examine structures in detail. Alternatively, the size in x-direction may be several pixels/voxels, e.g. 10 to 256 voxels, so that the output image is an output volume, wherein the size may be e.g. 0.5 cm to 2 cm, and which corresponds to a "thick-slab" transformation. A thick-slab reformation allows one to review the elongated anatomical structure, preferably the complete anatomical structure, e.g. the spine, but without the image being occluded by further anatomical structures.

Also, the desired resolution (corresponding to the grid size, i.e. how many pixels/voxels in each direction) of the output image may be freely selected.

The transformation may then be performed in reverse, i.e. from the reformatted image volume, to the original or input image volume. Thus, for each pixel in the output image, its relative coordinates with respect to the reformatted parametric curve may be determined, e.g. the distance from the curve and the position along the length of the curve. These relative coordinates may then be transferred to the (original) parametric curve, to thereby find the coordinates of the corresponding point within the image space of the original 3D ultrasound image volumes. Since this point may not be directly on the grid of the original image volumes, known re-gridding techniques such as first order interpolation may be used to calculate the voxel value in the reformatted image. In other words, once the transformation is defined, the transformation is directly applied on the grid of the output image. Each pixel of voxel in the output image volume maps into a location in the original 3D ultrasound image volume. From that location, intensity values are interpolated using an interpolation kernel, which may be 0th order, i.e. nearest neighbor, but usually would be first order, i.e. linear, or second order, corresponding to cubic, interpolation.

In another embodiment, a transformation matrix which transforms the (original) 3D ultrasound image volume to the reformatted image volume may be calculated, i.e. a forward transformation is performed. In this case, the re-gridding may be done on the grid of the output image, since a voxel of the input image may not map directly onto a pixel or voxel of the output image.

This reformatting is performed on each of the plurality of 3D ultrasound image volumes, resulting in a plurality of reformatted image volumes, which, once fused with one another, present a single overview allowing for immediate assessment of the spine, appreciation of spine length, presence of each segment and any evidence of spinal compressing or spinal bifida.

In addition, the reformatting of the 3D ultrasound image volumes simplifies the problem of registering and fusing the reformatted image volumes with one another. The reformatted image volumes are registered with one another by determining the joining point of their respective reformatted parametric curves. Thereby, the registration is simplified because the candidate points for registering the reformatted image volumes are located on the respective parametric curves (the "original" parametric curves or preferably the reformatted parametric curves). In an embodiment, the joining point is determined by taking one point on the parametric curve of a first reformatted image volume (e.g. at a pre-determined distance from one end of the image volume, or at a pre-determined vertebra, or simply the end point of the parametric curve), and determining the corresponding point in the parametric curve of a second, adjacent but overlapping reformatted image volume. Thus, if the two adjacent reformatted image volumes are fused by overlaying these two joining points, the overlapping parts of the adjacent image volumes should match, so that the two image volumes are registered with one another. One could say, two adjacent reformatted image volumes are joint together at the joining points.

The joining point on the second reformatted image volume which corresponds to the joining point on the first reformatted image volume can be determined in various ways. In one embodiment, one may simply find the corresponding vertebra on the parametric curve of the second reformatted image volume. In another embodiment, the parametric curves (preferably before reformatting) of the first and second image volume are compared with one another and the best-fitting joining point found. In a further, preferred embodiment, the joining point may be determined using an optimization algorithm. Such optimization algorithm may for example vary the second joining point along the respective parametric curve(s), and for each position calculate a similarity metric between the overlapping part of the adjacent (reformatted) image volumes. Such similarity metric is preferably a measure for the goodness of the registration between the two image volumes. The optimization algorithm may then optimize said similarity metric, which depends on the position of the joining point on the parametric curves(s), for example by minimizing a (cost) function.

Since also the reformatted parametric curves are parametrized, the registration between the reformatted image volumes may be simplified into a registration parametrized along the arc length of the spine (i.e. along the parametric curve). Thereby, the search for the joining points of the parametric curves, is performed on a reduced dimensionality space, thereby reducing the complexity of a non-rigid registration by reducing the number of variates.

Accordingly, the proposed invention provides a novel method to enable complete visualization of the whole anatomical structure from multiple ultrasound volumes via contextual (e.g. spine) fusion and its presentation, e.g. in reformatted views for immediate appreciation of spinal defects. This further allows to derive automatically or semi-automatically parameters and anatomical objects (e.g. segmentations) from the reformatted image volumes for quantitative assessment. The reformatted image volumes may be presented in thin and thick slab views from two orthogonal directions. Thus, the invention allows e.g. for immediate appreciation of the presence of each of the spinal segments, their marking, the assessment of inter-vertebral distance, and the presence of fetal spine anomalies In an embodiment of the present invention the parametric curve may be generated by automatically or manually identifying control points on the elongated anatomical structure and fitting a parametric curve, in particular a spline function, to the control points. For example, the control points may be on the center of each or some of the segments of the spine.

The segment of the spine may be a single vertebra. The control point may be positioned at the center of the body of the vertebra. Alternatively, the control point may be positioned at the vertebral foramen of the vertebra. This is advantageous when using a semiautomatic identification of the control points, because the vertebral foramen may be easily detected within the 3D ultrasound image volumes, e.g. by thresholding. A control point may be identified at each vertebra or only at every second, third or fourth vertebra.

Once the control points are identified, the parametric curve may be fitted to the control points so as to obtain a smooth curve. Advantageously, splines may be used as the parametric curve, because of their simplicity of construction, their ease and accuracy of evaluation, and their capacity to approximate complex shapes through curve fitting and interactive curve design. Curve fitting may either require an exact fit to the control points, or an approximate fit. Preferably, the parametric curve is continuous and differentiable, but it may also be a piecewise linear function connecting the control points.

The control points may be manually placed on the center of each of the segments of the spine (C1-7, T1-12, L1-5, S1-5) using a pointing device, for example. This can be done by a user while looking at a sectional view through the image volume, e.g. a Multiplanar Reconstruction (MPR) view displayed on a screen. Alternatively, the control points may be generated at the centerline of the spine automatically, for example using control point estimation using AI (e.g. control point regression). In the latter case, a user may check the control points, e.g. whether they are correctly placed at the center of each segment, and may manually change a position thereof, wherein this procedure (automatic selection of control points and control by a user) is an example of a semi-automatic selection.

Once the parametric curve (e.g. the spline) is generated, the reformation may be done by using the parametric curve.

In an embodiment, the reformatted image volumes, or the fused reformatted image volumes, may be visualized by aggregating its intensity values across a viewing direction using a compositing function. In a useful embodiment, the viewing direction is the third or depth axis (x-axis), which is orthogonal to the first two axes, i.e. it is orthogonal to the longitudinal direction of the elongated anatomical structure. In the example of spine, the viewing direction may advantageously be orthogonal to the length of the spine as well as to the ribs. However, it may also be along the second or y-axis, resulting in a sagittal view. The compositing function can be maximum intensity, resulting in a maximum intensity projection (MIP), mean intensity, or a standard volume rendering front to back accumulation, for example a volumetric ray tracing (VRT). The aggregated intensity values may be displayed to a user on a screen or other display device, which may be part of a medical ultrasound device.

Arc-Length Reformation

According to a first embodiment of reformatting each 3D ultrasound image volume, a so-called arc length reformation of the elongated anatomical structure is performed. In this type of reformation, the anatomical structure (e.g. the spine) is flattened out and pulled taut. Accordingly, in the reformatted coordinate system, the fetus appears straightened along its left-right axis and along its anteroposterior axis. In particular, in this embodiment of arc-length reformation, the step of reformatting each 3D ultrasound image includes applying a transformation, which unwarps the parametric curve, so as to straighten it using a local coordinate system comprising or consisting of two axes orthogonal to the tangent of the curve, so that the reformatted image volumes comprise an arc-length reformation of the spine. With this reformation, the arc-length of the spine is preserved, and the reformatted parametric curve may be straight line. In other words, the parametric curve is straightened in two directions.

A local coordinate system is one that is applied at one point along the parametric curve. As the parametric curve is not straight before the reformation, the directions of the axes, as explained herein, are not the same in each local coordinate system. However, after the reformation, at least one axis is aligned for each local coordinate system, i.e. the parametric curve has been straightened along this axis. In the arc-length reformation, preferably both axes orthogonal to the tangent of the curve (the primary axis) are aligned.

In the arc-length reformation, the primary axis (z-axis) of the reformatted image volume is along the parametric curve that runs along the central neural tube of the spine, and which has been straightened and pulled taut. Thus, the primary axis corresponds to the tangent of the parametric curve. The secondary axis (y-axis) may be orthogonal to this curve in each local coordinate system, and parallel to the ribs, i.e. approximately in left-right direction of the fetus. Preferably, the arc-length reformation also takes account of the fact that the spine may have a torsion, i.e. the direction of the two axes orthogonal to the tangent of the parametric curve may not be the same in each local coordinate system. In other words, the secondary axis along which reformation is done is a "free axis", i.e. it rotates around the primary axis. The aim is for the second axis to be oriented such the widest portion of the spinous process is visualized. That is, the secondary axis is aligned so as to be in a plane with the widest portion of the vertebra. In other words, the secondary axis is preferably parallel to the rib-cage, i.e. in left-right direction.

In an embodiment, the orientation of the second axis may be determined by first finding the ribcage of the fetus by thresholding. If control points along the centerline of the spine are known, a local thresholding may be done around these points. This may identify at least some parts of the ribs which extend from the spine roughly in a horizontal right-left direction. Thereby, a set of points may be found which are located on the spine and ribcage. This set of points may be analysed to find the left-right direction overall, or the secondary axis (y-axis) for each local coordinate system. For example a straight line may be fitted to each rib, as determined by thresholding. Alternatively, this may be done by Principal Component Analysis of the set of points, which may be visualized as fitting an ellipsoid to the set of points—therein, the principal axis will be along the spine, and the second axis will provide the required direction of the y-axis. Therefore, the reformatted image volume and/or the fused image may comprise a primary axis that corresponds to the parametric curve, and a secondary axis which is locally orthogonal to the primary axis and parallel to the ribs.

Accordingly, in the arc-length reformation, the reformation of the spine is performed along its arc length, thereby also orienting the spine along the y-axis. Scrolling through slices of this reformation allows one to traverse anterior to posterior (with the spine flattened out and pulled taut). A thick slab reformation with a MIP (Maximum intensity projection) or VRT (Volumetric ray tracing) may present a single overview allowing for immediate assessment of the spine, appreciation of spinal length, presence of each segment and any evidence of spinal compression or spinal bifida. These slabs may be presented in coronal or sagittal views. This reformation may be done automated through directional centerline tracing of the spine end to end with manual overwrite for reducing error accumulation.

In the next step, fusion of the spine from multiple ultrasound acquisitions is done. After the arc length reformation of the spine, a semi-automatic fusion may be achieved by translating one volume onto another along the primary axes of each reformatted volume. The efficiency of the joining is very high, because the search for the joining points of the parametric curves is performed on a reduced dimensionality space, where the search space may be limited to one dimension (along the parametric curve). Accordingly, the variate may be just the translation vector along the reformatted parametric curve. Therefore, the present embodiment provides a highly robust and efficient registration of different 3D volume images.

Curvature Preserving Reformation

According to a second embodiment of reformatting each 3D ultrasound image volume, a curvature-preserving reformation of the elongated anatomical structure is performed, wherein unwarping (straightening) of the elongated anatomical structure is done along one axis alone, in preferably along an axis orthogonal to a reference plane of the anatomical structure. The reference plane may be determined by fitting a plane to the anatomical structure, in case of a fetus to a part of the fetus for example to the spine, e.g. to anatomical landmarks on the spinous processes, and/or to the ribcage. According to this curvature-preserving reformation, the step of reformatting each 3D ultrasound image volume includes applying a transformation, which unwarps the parametric curve in a local coordinate system along one axis, which is orthogonal both to the tangent of the parametric curve, and to the reference plane, so that the reformatted image volumes comprise a curvature-preserving isometric reformation of the anatomical structure. Such reference plane is not warped, but planar. The reference plane may be a least-squares fitting plane of the elongated anatomical structure or a larger anatomical structure to which is belongs. In the case of a spine, it may be a plane fitted to anatomical landmarks on the spinous processes. In an embodiment, the reference plane is a canonical coronal plane of the fetus. This reformation unwarps the spine by flattening the "waves" of the spine orthogonal to its reference plane. The total length of the spine is preserved. This can be likened to the total path a ship has to take including the motion up and down the waves, wherein the total path is flattened out onto a planar view, so that the sideways curves (which would correspond to the spine curvature in the left-right axis) are preserved. This reformation is useful to analyse conditions such as kyphoscoliosis.

Such reformation is comparable to a curved planar reformation (CPR), in particular a stretched CPR, as described in the article "CPR—Curved Planar Reformation" by Armin Kanitsar, Dominik Fleischmann et al. in a paper presented at IEEE Visualization 2002. In CPR, a longitudinal structure, such as a vessel, is re-sampled onto a surface, which is defined by the centerline of the vessel and by an additional vector, which is called the vector-of-interest. In "stretched CPR", the surface defined by the vessel centerline and the vector-of-interest is curved in one dimension and planar in the other one. Stretching the curved dimension results in a plane showing the tubular structure in its entirety without overlapping. In the curvature-preserving reformation of the present invention, this surface is termed a "virtual carpet" that the elongated anatomical structure lies on. One axis of the reformatted view of the spine is the line that runs along the length of the carpet along the principle axis of the elongated anatomical structure, in particular along the control points. The other axis of the reformatted view is orthogonal thereto, but is not a free axis anymore, but is the same for each point along the parametric curve and in each local coordinate system. Preferably, the other axis of the reformatted view is orthogonal to the primary axis and lies within the reference plane. The virtual carpet may be generated given the parametric curve and a 3D image volume.

In the curvature preserving reformation of the present embodiment, measurements in the reformatted volume are isometric. Generally, in an isometric view a distance between two points corresponds to the real distance between said points. That is, in the reformatted volumes of the present embodiment measurements may be taken. A thick slab reformation with a MIP or VRT may present a single overview allowing for immediate assessment of the spine and its curvature, allowing assessment of kyphoscoliosis, appreciation of spinal length, presence of each segment and any evidence of spinal compression or spinal bifida. Further thin slab reformations may allow one to examine structures in detail.

In a preferred embodiment of the curvature-preserving reformation of the elongated anatomical structure, the elongated anatomical structure is flattened onto a reference plane, which is a least-squares fitting plane. The least-squares fitting plane is fitted to the elongated anatomical structure, e.g. to the control points (e.g. the control points in the center of each or some of the segments of the spine) and/or anatomical landmarks on the spinous processes, and/or to the ribcage, preferably a segmentation of the ribcage of the fetus. The ribcage segmentation is relatively simple to obtain by a simple thresholding method. Please note that the spine is not projected onto this least-squares reference plane, but the transformation is such that the total length of the spine is preserved, as the spine is flattened and stretched onto the least-squares fitting plane.

For example, after a parametric curve (e.g. spline) is determined as outlined above, the reference plane or least-squares fitting plane defines the primary and secondary axes, i.e. the axis vectors. Thereby, a transformation can be defined algebraically, and applied to the grid of the output image, wherein each voxel in the output image volume maps onto a location in the original ultrasound image volume.

Registration and Fusing

Using either of these reformations (arc-length reformation of curvature-preserving reformation), the portions of the spine may be fused automatically or semi-automatically, by registering and fusing overlapping reformatted image volumes with one another. By performing the above-described reformations, automatic registration algorithms are made more robust than in the prior art, by reducing its number of variates. In one embodiment, the only variate is the translation vector (joining point) between the reformatted parametric curves from the pair of reformatted image volumes to be registered. This allows for rigid registration of one reformatted image volume with one another. In another embodiment, further variates are the locations of the control points, e.g. control points on the segments of the spine, which are used for fitting the parametric curves thereto. In further embodiments, the variates are the curve parameters of a parametric curve (such as a spline) that fits the spine in both volumes. This embodiment also improves the fit of the parametric curve fitted to the spine, along with the registration. This may for example be performed by an optimization algorithm which includes the curve parameters as well as the joining point in the parameters which are varied in the process of e.g. minimising a cost function. Accordingly, the registration may be parametrized along with the variates of the spline that fits the spine on both of the pair of reformatted image volumes. This allows for non-rigid registration of one spine portion (reformatted image) with another.

According to one embodiment, the step of registering two (overlapping) reformatted image volumes may include the steps of:
selecting a joining point of their respective reformatted parametric curves along the parametric curves,
computing a similarity metric between the overlapping parts of the two reformatted image volumes, when joined at the joining point,
translating the joining point along the reformatted parametric curve and again computing the similarity metric.

The last step (translating and again computing) may be repeated several times. The same registration and fusion process can be applied for the arc-length reformatted image volume and the curvature preserving reformatted image volumes.

The joining point is one point on each of the two parametric curves belonging to each of the two overlapping or adjacent image volumes, namely the points at which the two parametric curves will join, so as to produce one continuous parametric curve (e.g. spline) through both reformatted image volumes. The joining point can be parametrized as a translation along this parametric curve. The joining point may be the location at which the two (reformatted) parametric curves may be connected in order to form a continuous parametric curve fitted to the spine. According to this embodiment, the parts of the reformatted image volumes which overlap are compared with one another for example by calculating a similarity metric to evaluate Goodness of Fit of the registration. This is followed by translating the joining point (and optionally varying further variates as described herein), and again computing the similarity metric. This step may be repeated (preferably iterated) several times, until a good similarity metric has been found. Preferably, the similarity metric is optimized, i.e. a maximum of the similarity metric is determined, e.g. using an optimization algorithm or optimizer. The similarity metric may be optimized by minimizing a cost function, wherein the cost function defines the effort to register two reformatted volumes.

The similarity metric used in the registration process may be a mean square error metric, or any similarity metric typically used in image registration, such as "normalized cross correlation", "mutual information", etc. The step of (preferably several times) translating and again computing the similarity metric finds the variates that maximize the similarity metric. The variates may be the joining point for a continuous spline through the original and/or reformatted image volumes, and optionally the curve parameters. A suitable optimizer may for example be a gradient descent optimizer. The likelihood of finding the minimum in the optimization process is proportional to the dimensionality of the search space, and therefore, by reducing the dimensions of the search space (i.e. the number of variates), the registration process becomes more robust.

During the step of fusing, the overlapping parts of a pair of reformatted image volumes which have been registered with one another, may be used to calculate the voxels in the fused image either by using the voxel intensity values from one of the pair of overlapping image volumes, or by combing the intensity values of the two overlapping parts. In an embodiment, this is achieved by "fading" one reformatted image volume into the other, i.e. the weighting of the two reformatted images in the combined intensity value changes along the primary axis, so that one image is slowly "blended" into the other.

Further, during the registration and fusion, an interpolator may be used. The interpolator may be used to re-grid a source image (i.e. a first reformatted image) onto a target image (i.e. a second reformatted image) grid. In more detail, a similarity metric may be evaluated over all voxels of the target image grid. At each voxel location, given the current transformation (joining point), the location in the source image has to be identified. These may fall on non-grid locations i.e. in-between voxels in the source image. An interpolator (usually 1st order) may be used to obtain in-between voxel (subvoxel) intensities from the source image.

In an embodiment of the present invention the step of registering two reformatted images may include weighting the similarity metric based on a distance from the parametric curve so as to give prominence to features close to the spine. Thereby, a high quality registration of the spinal anatomy may be achieved, whereas local deformations away from the spine, such as that of the fetal limbs or the maternal habitus, may be ignored. Preferably, weighting may be applied so that values in the vicinity of the centerline are given a larger weight in the metric. The distance from the parametric curve may be a distance along a direction that is orthogonal to the parametric curve. In other words, there may be defined a radius that defines a circular surrounding the parametric curve in which radius the values may be given a larger weight in the metric. The radius may be in a range between 1 cm and 10 cm, preferably 1.5 cm to 5 cm. In the same way the cost function (metric) may be also weighted based on the distance from the parametric curve giving prominence to the features along the parametric curve.

In a further embodiment of the present invention, the step of registering of two reformatted images may include re-fitting of the parametric curves of the reformatted image volumes e.g. to the depicted portions of the elongated anatomical structure on the fused image, or on the reformatted image volumes, and wherein the step of reformatting the 3D ultrasound image volumes is executed again using the re-fitted parametric curves.

In order to improve the registration between two adjacent image volumes, one may change the curve parameters as well as the joining point along the parametric curve. The reformatted 3D ultrasound image volumes may be re-generated at a next repetition/iteration based on the changed curve parameters, a similarity metric may be then computed again and so on. This could be done with either the arc length or the curvature preserving reformation. In an embodiment, the control points to which the parametric curve may be fitted may be shifted, in particular shifted over a spine segment (e.g. the vertebra), during the registration process. Subsequently, the parametric curve may be fitted again to the control points. Thereby, the parametric curve fit is improved along with the registration. In an embodiment, this step may be carried out using an optimizer, for example, a gradient descent optimizer.

When using an optimizer, the complexity of the optimization process and the likelihood of finding a maximum of the similarity metric (minimum of cost function) is proportional to the dimensionality of the search space. Transformations in non-rigid fusion are generally of high dimensionality. In the present embodiment, a non-rigid fusion may be executed using just a handful of parameters that define the parametric curve that fits the spinal anatomy. Therefore, the process may be highly efficient because the dimensionality of the problem may be reduced as compared to generally known non-rigid fusion problems.

In addition, since the metric may be evaluated over just the reformatted images being visualized, the number of voxels visited at each iteration of the metric evaluation may be small, making the process even faster.

In an embodiment, the method may further include a step of automated identification of landmarks on the elongated anatomical structure, for example so as to identify each vertebra and/or quantify a start and an end point of each vertebra so as to identify a vertebral body. Preferably, this step is performed on the reformatted volumes, or on the fused image.

In one use case, evaluating an integrated intensity maximum orthogonal to the parametric curve may output the locations of the spinal segments and the inter-vertebral distance.

Given the arc length reformation of the spine from multiple acquisitions, the present embodiment may automatically identify landmarks for identifying each vertebrae. This may be conveniently done on the straightened view, where the segmentations need only be searched in one parametric space (i.e. along the primary axis). They may then be displayed on the other views. Further, several measures may be derived such as the inter-vertebral distance, lateral intra-pedicle distance. Skin line can also be automatically detected and any deviation highlighted (missing skin or abnormal curve/bump) in a sagittal view.

In a still further embodiment, the method may further include a step of automatically performing quantitative measurements on the fused image, wherein in particular the inter-vertebral distance, lateral-pedicle distance and/or the skin line are automatically determined.

In another aspect of the present invention a computer program is provided, comprising program code instructions which, when executed by a processor, enables the processor to carry out the inventive method.

The invention is further directed to a computer-readable medium comprising an above-defined computer program. The computer-readable medium may be any digital data storage device, such as a USB-stick, CD-ROM, SD-card, SSD-card, hard disc. Naturally, the computer program need not to be stored on such a computer-readable medium to be supplied to customers, but may be downloaded from a distant server or cloud, e.g. over the internet.

In a third aspect of the present invention an image evaluation device is provided, configured to perform an embodiment of the inventive method, the evaluation device comprising:
- a data storage derive for receiving a plurality of 3D ultrasound image volumes, each image volume depicting at least a portion of an elongated anatomical structure;
- a computing unit for performing the above method, and
- a screen for displaying the at least one reformatted image volume, or the fused image.

The data storage device is configured to store data such as a hard disk drive. The computing unit may be a processor (e.g. CPU or GPU) capable of performing the above method. The screen may be a display that may display one or more images generated using the above method. Further, the screen may be the screen of an ultrasound device. In addition, the screen may be a touch sensitive screen which may be used as interface for inputting commands. For example, the user may set the above control points by tapping on a specific location on the screen.

In a further aspect of the present invention an ultrasound system is provided, comprising:
- a probe configured to obtain 3D ultrasound volumes, and
- the above image evaluation device.

The probe is preferably a 3D transducer which may directly obtain 3D ultrasound image volumes via beam steering and/or beamforming.

All features and advantages mentioned in connection with the method are also applicable on the computer program, the image evaluation device and the ultrasound system, and vice versa.

BRIEF DESCRIPTION OF THE DRAWINGS

The invention shall now be illustrated by means of particular embodiments with reference to the attached drawings, in which.

DESCRIPTION OF EMBODIMENTS

Throughout the figures, the same or corresponding features/elements of the various embodiments are designated with the same reference numbers.

A digital image (e.g. an ultrasound image) is composed of digital representations of one or more objects (e.g. the spine). The digital representation of an object is often described herein in terms of identifying and manipulating the objects. Such manipulations are virtual manipulations accomplished in the memory or other circuitry/hardware of a computer system. Accordingly, is to be understood that embodiments of the present invention may be performed within a computer system using data stored within the computer system. For example, according to various embodiments of the present invention, electronic data representing a 3D ultrasound image volume is manipulated within a computer system in order to reformat the image to visualize the spine.

Figure 1:
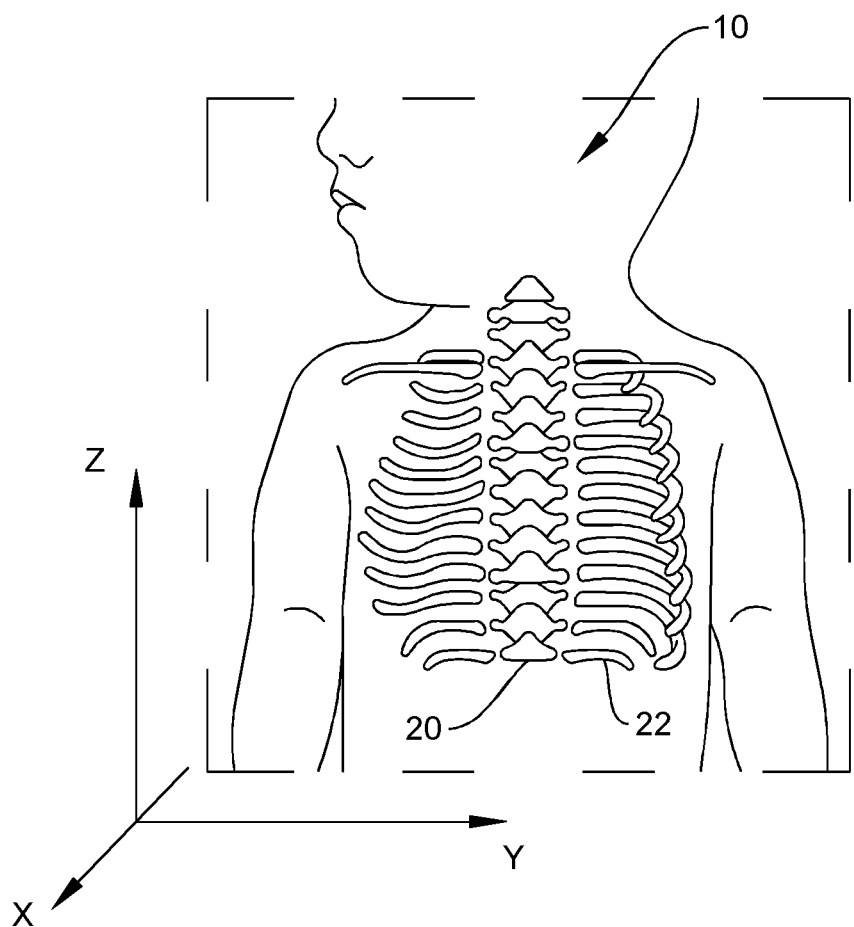
FIG. 1 shows a schematic and perspective illustration of a fetus and its spine and ribcage.

FIG. 1 is a schematic and perspective illustration of a fetus 10 as viewed from the front. The spine 20 and ribcage 22 of the embryo 10 (i.e. fetus) is highlighted. In addition, a coordinate system is illustrated in which a z-direction runs along the length of the spine, corresponding to a longitudinal axis, and the y-axis corresponds to the left-right or horizontal axis. In particular, it is the horizontal axis of the least squares fitting plane to the ribcage. The x-direction corresponds to the anteroposterior axis.

Figure 2:
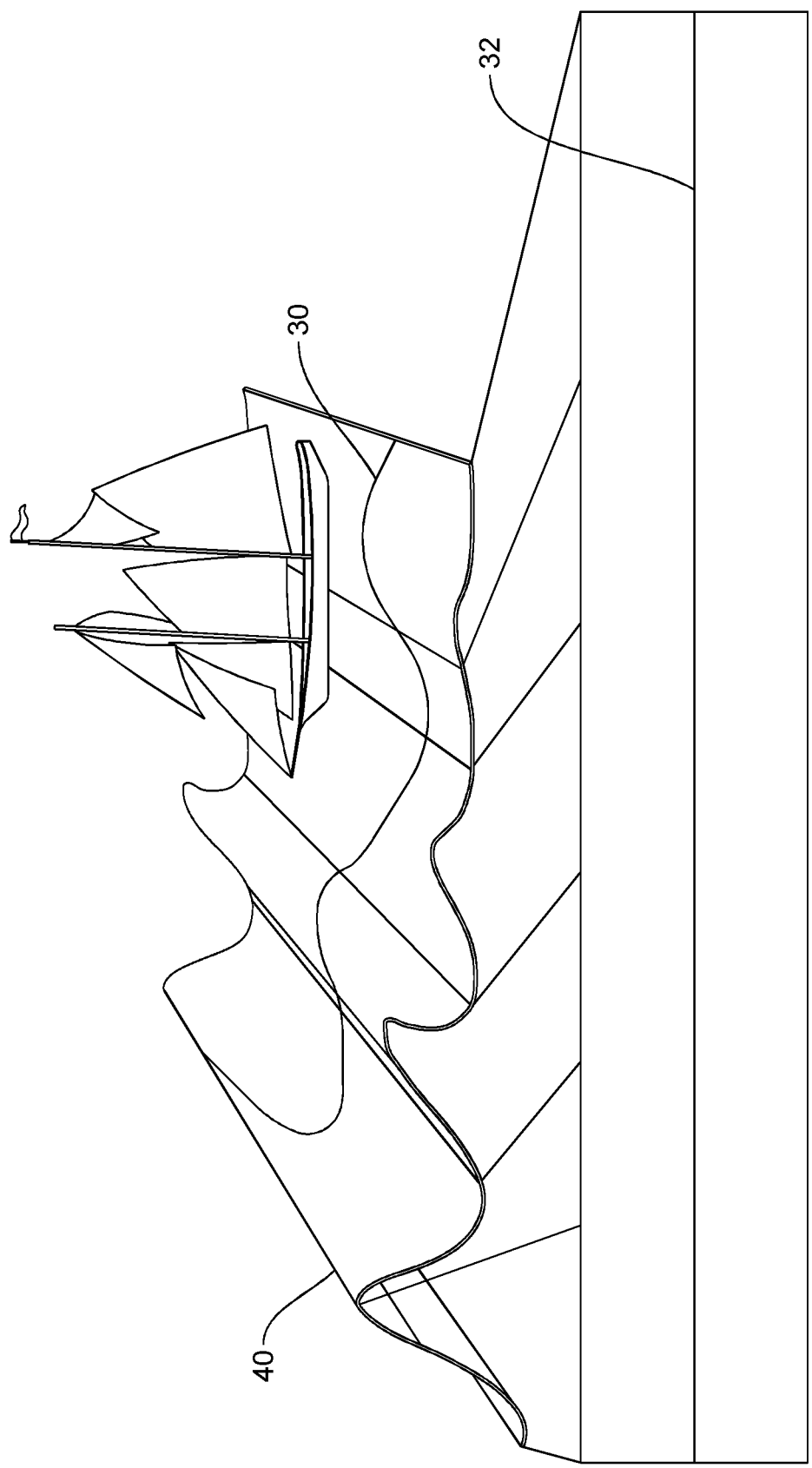
FIG. 2 shows an illustration of an arc-length reformation.

FIG. 2 illustrates the principle of arc-length reformation. The top part of the figure shows the virtual carpet 40, on which the spine lies. The virtual carpet is a warped surface 40 which follows the curvature of the parametric curve 30, which is shown as a line below the ship. The virtual carpet 40 may also be also twisted somewhat around the parametric curve 30, so that the y-direction (i.e. the axis orthogonal to the tangent of the parametric curve and lying within the virtual carpet 40) in each local coordinate system is parallel to the spinous processes. In the arc-length reformation, the parametric curve is preferably completely straightened and pulled taut, to result in a straight reformatted parametric curve 32.

Figure 3:
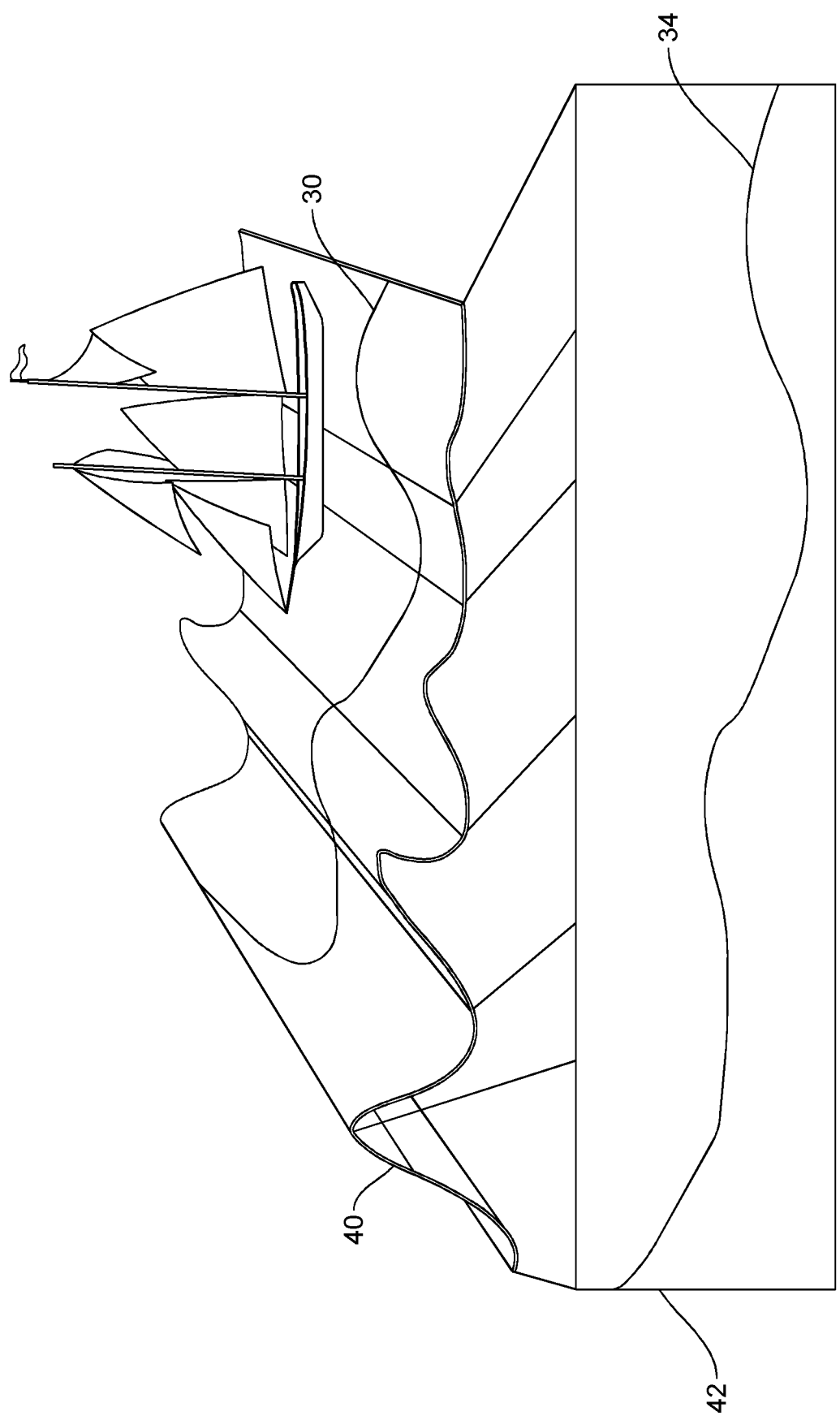
FIG. 3 shows an illustration of a curvature-preserving reformation, FIG. 4 a flow diagram illustrating the steps e according to an embodiment of the inventive method.

FIG. 3 illustrates the principle of a curvature preserving reformation. The top part of the figure again shows the virtual carpet 40, on which the spine lies. The virtual carpet 40 is straight in one direction and follows the curvature of the parametric curve 30, which is shown as a line below the ship, in the other direction. In other words, the virtual carpet 40 is curved in one dimension, and planar in the other one. In a preferred embodiment, the direction in which the carpet is plane, is parallel to the reference plane, in particular a least-squares fitting plane to the spine or ribcage. In the curvature-preserving reformation, the spine is unwarped by flattening the "waves", i.e. the virtual carpet is pulled taut to result in the re-sampled surface 42 shown in the lower part of the figure. Therein, the reformatted parametric curve 34 preserves the total length of the parametric curve 30, as are the curves of the spine in the direction in which the virtual carpet 40 is planar. Unwarping is along one axis alone, which is preferably the axis orthogonal to the least-squares fitting plane.

Figure 4:
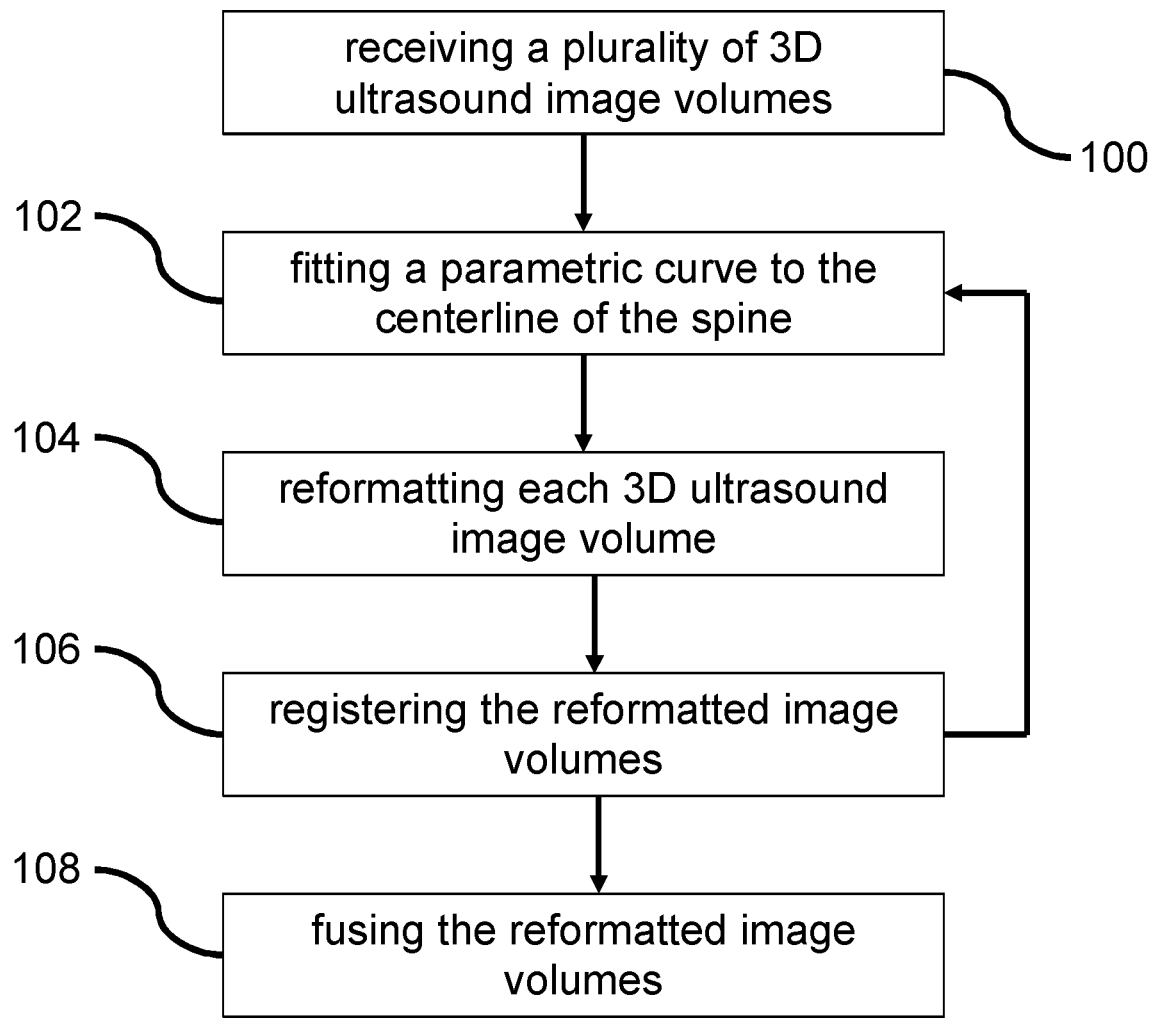

FIG. 4 is a flow diagram illustrating the steps of an embodiment of the computer-implemented method for visualization of a fetal spine using ultrasound according to the present invention. In Step 100, a plurality of 3D ultrasound image volumes, each image volume depicting at least a portion of the fetal spine of a fetus are received. In the present embodiment received means that the 3D ultrasound image volumes are loaded on a computer on which the inventive method is executed. 3D ultrasound image volumes may be acquired in the same US examination, and consecutive image volumes along the fetal spine overlap by 10% to 50% of the image volume (or spine length). For example, there may be 2-10, preferably 3-7 3D ultrasound image volumes of the same fetal spine.

In step 102, on each 3D ultrasound image volume, a parametric curve is automatically or semi-automatically fitted to the centerline of the depicted spine portions. The parametric curve is defined by curve parameters. In one embodiment of the present invention, the user identifies the segments of the spine (e.g. the center of some of the vertebras) manually via a pointing device (e.g. cursor actuated by a mouse) on a screen, or by tapping on a touch screen 218. By tapping on the segment of the spine, the user defines control point, which may be a curve parameter of the parametric curve. The parametric curve fitted to the control points is displayed in real-time such that the user may decide whether it is necessary to correct the curve, or to identify further control points or not, so as to provide a parametric curve that follows the geometry of the fetal spine. In another embodiment, the spine segments may be identified automatically, e.g. by a segmentation.

In step 104, each 3D ultrasound image volume is reformatted by applying a transformation which straightens the parametric curve along at least one axis, so as to generate a plurality of reformatted image volumes and reformatted parametric curves. In an embodiment where the parametric curve fitted to the spine in step 102 is a spline that is continuous and differentiable, the reformation along at least one axis may be done implicitly. For example, in some embodiments, by differentiating the parametric curve in a desired direction, the reformation of the image volume may be derived in a straightforward manner in this direction.

Figure 5:
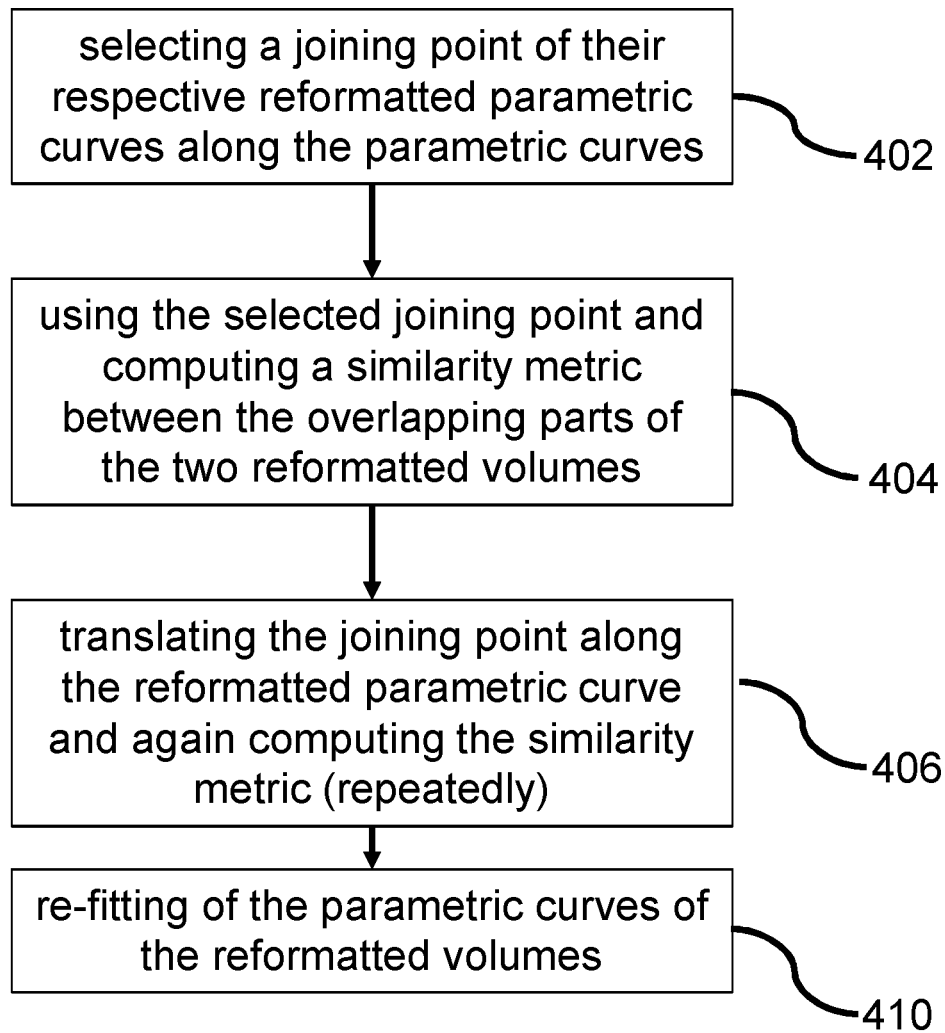
FIG. 5 shows a flow diagram illustrating the steps included in the step of registering the reformatted image volumes according to an embodiment of the present invention.

In step 106 the reformatted image volumes are registered with one another by determining the joining point of their respective parametric curves. In one embodiment, the 3D ultrasound image volumes adjacent to each other overlap about 10-50%, preferably 20-40% percent of their size, thereby allowing registration of the overlapping parts of the image volumes. Rather than the original 3D image volumes, the reformatted image volumes are registered with one another. This reduces the complexity of a non-rigid registration by reducing the number of variates. Preferably, the similarity metric is also weighted based on the distance from the parametric curve, giving prominence to features along the spinal anatomy. In a useful embodiment, the parameter space of a cost function, which is minimized during the registration step 106, also includes the curve parameters of the parametric curve in the two reformatted image volumes. Accordingly, in step 106, the parametric curve may be changed (re-fitted) and thus the reformatting of step 104 may be carried out again to further improve the registration process. This is indicated by an iteration of steps 102, 104 and 106. Finally, once the registration 106 has resulted in determining the joining point between the reformatted parametric curves, and optionally re-fitted curve parameters, the reformatted image volumes are fused with one another In FIG. 5, a flow diagram illustrating the steps included in the step of registering the reformatted image volumes according to an embodiment of the present invention is displayed.

In step 402 a joining point of the respective reformatted parametric curves of the reformatted image volumes along the parametric curves is selected. In step 404, a similarity metric between the overlapping parts of the two reformatted volumes when joined at their respective joining points is computed. In step 406 the similarity metric is repeatedly computed after translating the joining point along the reformatted parametric curve. The similarity metric may be weighted based on a distance from the parametric curve so as to give prominence to features close to the spine. In step 410 the parametric curves of the reformatted volumes are re-fitted, and wherein the step of reformatting the 3D ultrasound volumes is executed again using the changed parametric curves (refer also to the arrow in FIG. 2 between step 106 and step 102 which indicates the iteration).

Figure 6:
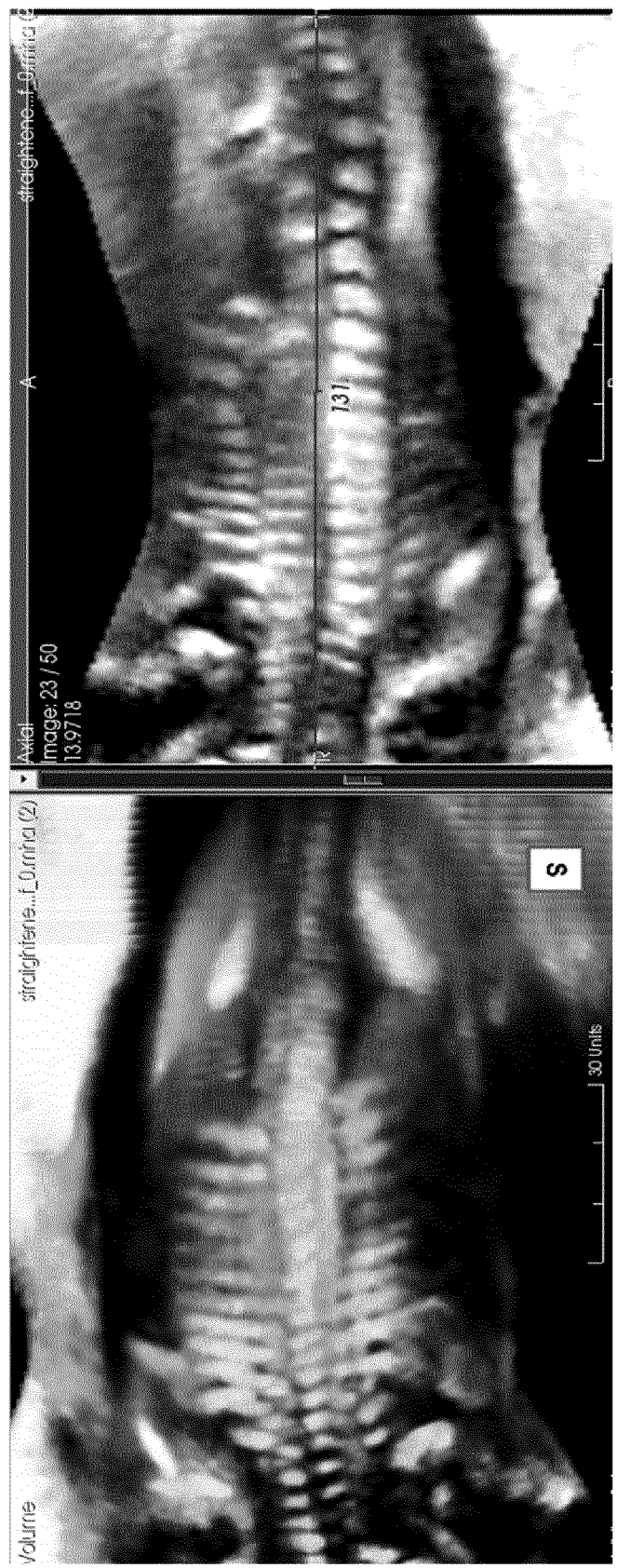
FIG. 6 shows fused images of a fetal spine obtained by arc-length reformation.

FIG. 6 shows two reformatted ultrasound images, in which the spine is unwarped along its arc-length to generate the reformatted volume. A thin-slab reformation or a slice of a reformatted image volume is shown on the right. A volume rendering of the reformatted image volume orthogonal to the arc-length is shown on the left. That is, the spine is "pulled taut" along its length. The reformatted volume is generated along the primary or (in this representation) horizontal axis which is the arc length of the spine. The vertical axis in FIG. 5 corresponds to the y-axis as described herein. A thick slab visualization via MIP (Maximum intensity projection) or VRT (Volumetric ray tracing) of such a reformation shows what the spine would be if the baby were lying flat on the back, without bending the spine as it is typical in the uterus. This allows for immediate appreciation of presence of each of the spinal segments (cervical, thoracic, lumbar and sacral), marking of all segments of the spine from top to bottom sections, assessment of inter-vertebral distance and presence of spina bifida.

Figure 7:
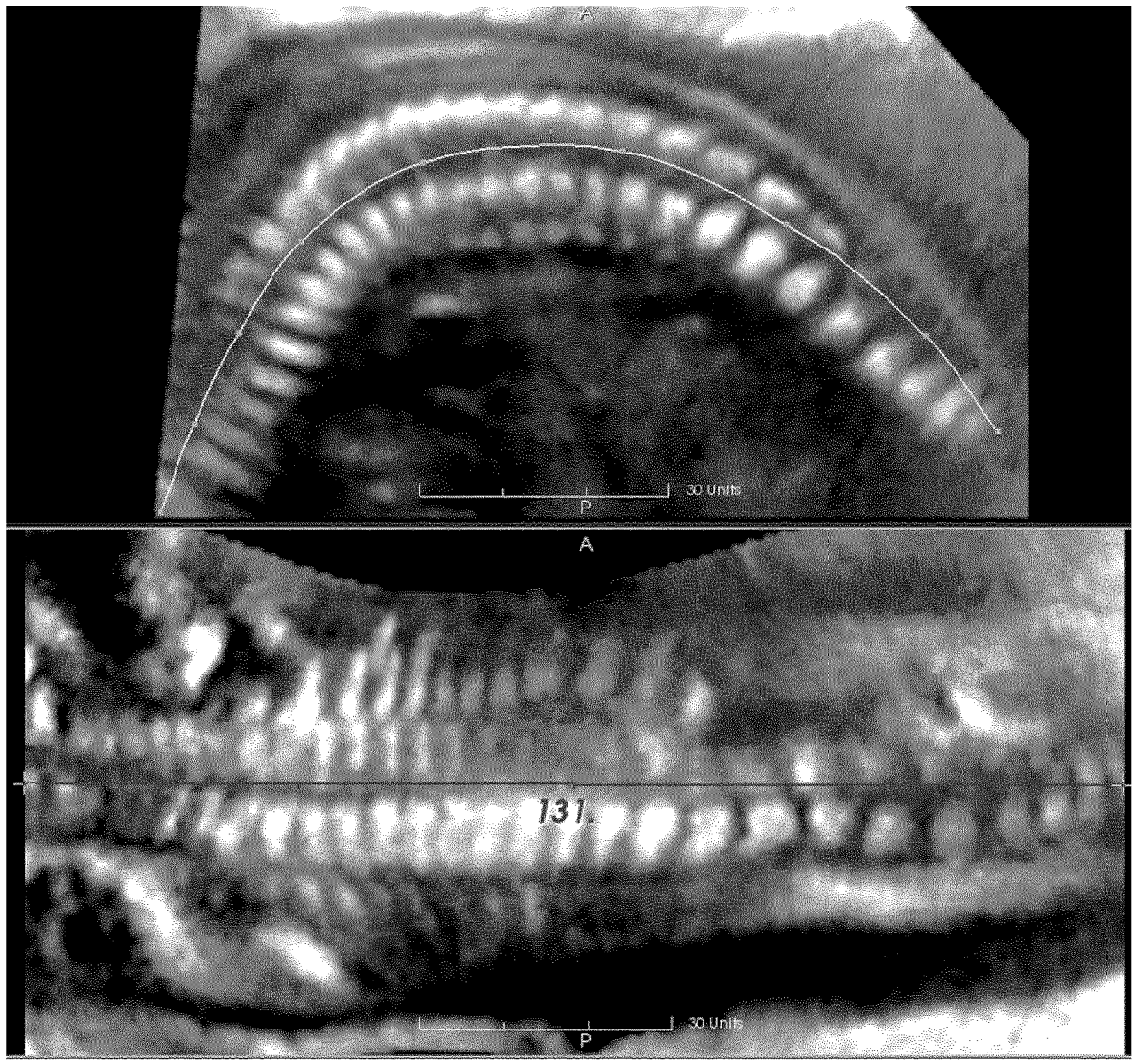
FIG. 7 shows two ultrasound images: the one at the top is obtained by a curvature preserving reformation, the one at the bottom is obtained by an arc length reformation.

FIG. 7 shows two ultrasound images: the one at the top is obtained by a curvature preserving reformation, the one at the bottom is obtained by an arc length reformation. The curvature preserving reformation of the spine in the above image shows the bends in the spine. The reformatted parametric curve is overlayed on the image. Unwarping is done along one axis alone, which is the axis orthogonal to the least squares fitting plane of the spine points (e.g. control points). In the curvature preserving reformation in the upper image, the spine is unwarped by flattening the "waves" of the spine orthogonal to its least-squares fitting plane. The total length of the spine is preserved. All measurements on the displayed view are also preserved. Therefore, the view is isometric.

In the second trimester, the spine can often not be scanned in a single 3D view. At least two views may be required to cover the whole spine. Between two volumes, the spine may be non-rigid. Sources of this can be motion of the baby within the uterus. In an anterior spine presentation, it can also be due to probe pressure which can cause a deformation. The probe pressure itself may induce baby movement. Therefore, a registration and fusion of the individually captured 3D ultrasound image volumes is necessary.

Given the two acquisitions covering two portions of the spine, the non-rigid registration between two image volumes (which typically involves a large parameter space) can be simplified into a registration parametrized along the spine (i.e. along the parametric curve) via the reformatted volumes. In one embodiment in which the arc-length reformation is generated, the registration can be reformulated, such that the variate to be determined is the translation vector or transformation along the primary axis between the two reformatted volumes. In another embodiment in which the curvature preserving reformation is generated, the registration may be parametrized along with the variates of the low dimensional parametric curve, e.g. splice, that fits the spine. This jointly optimizes the parametric curve that fits the spine along with the transformation that fuses the two volumes themselves. Again, because this is parameterized along the parametric curve (i.e. along the spine), the registration is inherently non-rigid. Therefore, the search space for registration is limited based on parametrizations for the spine and the clinical problem at hand, vis-à-vis, the visualization of the spine. Further, in case the registration of arc length reformations is carried out first and thus the translation transformation between the two reformatted volumes is determined during the non-rigid registration, this information may be also used during the non-rigid registration of two curvature preserving reformations. Therefore, the latter method may exhibit a further improved efficiency.

Figure 8:
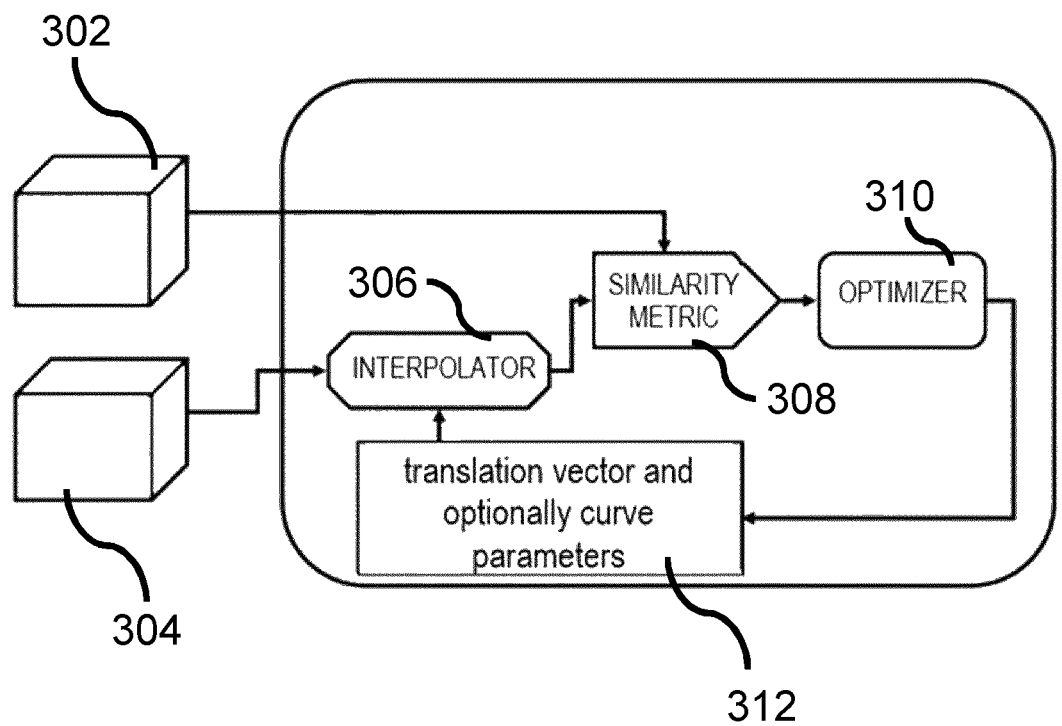
FIG. 8 shows a block diagram illustrating the iterative process during the registering of at least two 3D ultrasound image volumes.

Accordingly, FIG. 8 shows the non-rigid registration method of the present embodiment. Two reformatted overlapping image volumes 302, 304 are input to the method, wherein, assuming a particular translation vector between the parametric curves (resulting in a particular joining point), the similarity metric 308 between the overlapping parts of the two reformatted image volumes 302, 304 is calculated. This may require the use on an interpolator 306, because the grid points of the two image volumes may not coincide with each translation vector. The similarity metric 208 is input to an optimizer 310 which optimizes the similarity metric by varying the translation vector and, in some embodiments, also the curve parameters of the parametric curve 312. With the new translation vector, a new similarity metric 308 is calculated using the interpolator 306, until a maximum of the similarity metric 308 has been reached, as determined by the optimizer.

Figure 9:
FIG. 9 shows an ultrasound image in which an automated identification of spinal segments for each of the Cervical, thoracic, lumbar and sacral groups is carried out and displayed.

FIG. 9 shows an ultrasound image in which an automated identification of spinal segments for each of the Cervical, thoracic, lumbar and sacral groups is carried out and displayed. The different groups may be visualized with different indicators. In the present embodiment there are used pentagons and circulars to indicate different groups of vertebras. Please note that not each group is identified in FIG. 9. The automated identification of the landmarks or identification of each vertebra is conveniently done on the straightened view, i.e. the arc-length reformation, where the segmented image need only be searched in one parametric space (along the primary axis, i.e. horizontally in the displayed images). They may then be displayed on the other views, as in FIG. 9. From this, several measures are also derivable, such as the inter-vertebral distance, lateral intra-pedicle distance, etc. Skin line can also be automatically detected and any deviation highlighted, such as missing skin or abnormal curve/bump, e.g. in a sagittal view.

Figure 10:
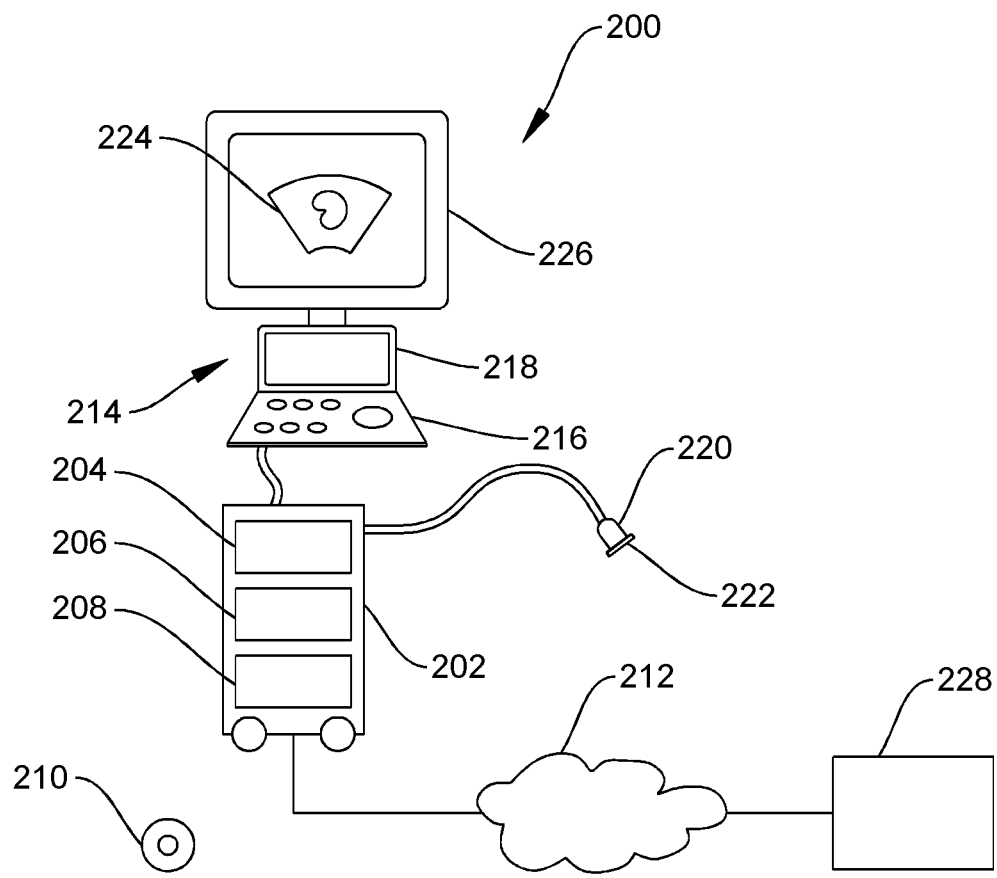
FIG. 10 a schematic representation of the system according to an embodiment of the invention.

FIG. 10 is a schematic representation of an ultrasound system 200 according to an embodiment of the invention and configured to perform the inventive method. The ultrasound system 200 includes a usual ultrasound hardware unit 202, comprising a CPU 204, GPU 206 and digital storage medium 208, for example a hard disc or solid-state disc. A computer program may be loaded into the hardware unit, from CD-ROM 210 or over the internet 212. The hardware unit 202 is connected to a user-interface 214, which comprises a keyboard 216 and optionally a touchpad 218. The touchpad 218 may also act as a display device for displaying imaging parameters. The hardware unit 202 is connected to an ultrasound probe 220, which includes an array of ultrasound transducers 222, which allows the acquisition of 3D ultrasound image volumes 224, for example B-mode images, from a subject or patient (not shown), preferably in real-time. 3D ultrasound images 224 acquired with the ultrasound probe 220, as well as reformatted or fused images generated by the inventive method performed by the CPU 104 and/or GPU, are displayed on screen 226, which may be any commercially available display unit, e.g. a screen, television set, flat screen, projector etc. Further, there may be a connection to a remote computer or server 228, for example via the internet 112. The method according to the invention may be performed by CPU 204 or GPU 206 of the hardware unit 202 but may also be performed by a processor of the remote server 228.

The above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

The invention claimed is:

1. A computer-implemented method for visualization of an elongated anatomical structure (20) using ultrasound, the method comprising the steps of:
   receiving a plurality of 3D ultrasound image volumes, each image volume depicting at least a portion of an elongated anatomical structure having a curved longitudinal extension;
   on each 3D ultrasound image volume, automatically or semi-automatically fitting a parametric curve to the depicted portion of the elongated anatomical structure along its longitudinal extension, the parametric curve being defined by curve parameters;
   reformatting each 3D ultrasound image volume by applying a transformation which straightens the parametric curve along at least one axis, so as to generate a plurality of reformatted image volumes and reformatted parametric curves;
   registering the reformatted image volumes with one another by determining the joining point of their respective parametric curves; and
   fusing the reformatted image volumes with one another to yield a fused image depicting the whole elongated anatomical structure or a larger portion thereof than the 3D ultrasound image volumes.

2. Method according to claim 1, wherein the reformatting of each 3D ultrasound image volume comprises the steps of:
   defining the dimensions and resolution of the reformatted image volume;
   for each voxel in the reformatted image volume, finding the corresponding coordinates of this voxel in the 3D ultrasound image volume by using the parametric curve and the reformatted parametric curve;
   calculating an intensity value of each voxel in the reformatted image volume by interpolating the intensity values of the voxels closest to said corresponding coordinates in the 3D ultrasound image volume.

3. Method according to claim 1 or 2, wherein the elongated anatomical structure is the spine of a fetus, and the parametric curve is fitted to a centerline of the depicted portion of the spine.

4. Method according to claim 1, wherein the parametric curve is generated by automatically or manually identifying control points on the elongated anatomical structure, in particular on the center of each or some of the segments of the spine, and fitting a parametric curve, in particular a spline function, to the control points.

5. Method according to claim 1, wherein the step of reformatting each 3D ultrasound image includes applying a transformation which unwarps the parametric curve so as to straighten it using a local coordinate system comprising two axes orthogonal to the tangent of the curve, so that the reformatted image volumes comprise an arc-length reformation of the elongated anatomical structure.

6. Method according to claim 3, wherein the reformatted image volume and/or the fused image comprises a primary axis that corresponds to a tangent of the parametric curve, and a secondary axis which is orthogonal to the primary axis and parallel to the ribs of the fetus.

7. Method according to claim 1, wherein the step of reformatting each 3D ultrasound image volume includes applying a transformation, which unwarps the parametric curve in a local coordinate system along one axis, which is orthogonal to a reference plane of the elongated anatomical structure, so that the reformatted image volumes comprise a curvature-preserving isometric reformation of the elongated anatomical structure.

8. Method according to claim 3, wherein the reference plane of the fetus is determined by fitting a plane to the spine and/or to anatomical landmarks on the spinous processes and/or to the ribcage of the fetus.

9. Method according to claim 1, wherein the step of registering two reformatted volumes includes:

selecting a joining point of their respective reformatted parametric curves along the parametric curves, using the selected joining point and computing a similarity metric between the overlapping parts of the two reformatted volumes, translating the joining point along one of the reformatted parametric curves and again computing the similarity metric.

10. The method of claim 9, wherein the step of registering two reformatted images includes weighting the similarity metric based on a distance from the parametric curve so as to give prominence to image features close to the elongated anatomical structure.

11. Method according to claim 1, wherein the step of registering the reformatted image volumes with one another includes re-fitting the reformatted parametric curves of the reformatted volumes.

12. Method according to claim 1, the method further including a step of automatically performing quantitative measurements on the fused image, wherein in particular the inter-vertebral distance, lateral-pedicle distance and/or the skin line are automatically determined.

13. A computer program comprising program code instructions which, when executed by a processor, enables the processor to carry out the method according to claim 1.

14. An image evaluation device comprising:
a storage for receiving a plurality of 3D ultrasound image volumes, each image volume depicting at least a portion of an elongated anatomical structure,
a computing unit for performing the method according to claim 1, and
a screen for displaying the reformatted image volumes, or the fused image.

15. An ultrasound system comprising:
a probe configured to obtain 3D ultrasound volumes, and
an image evaluation device according to claim 14.

* * * * *